United States Patent
Thomas et al.

[11] Patent Number: 5,976,193
[45] Date of Patent: Nov. 2, 1999

[54] METHOD COMPOSITION AND SYSTEM FOR REMOVING

[75] Inventors: Sherrie L. Thomas, Cedar Park; Paul F. Lane, San Antonio, both of Tex.

[73] Assignee: Cigone Enterprises, Inc., Cedar Park, Tex.

[21] Appl. No.: 09/054,558

[22] Filed: Apr. 3, 1998
(Under 37 CFR 1.47)

Related U.S. Application Data

[60] Provisional application No. 60/044,200, Apr. 8, 1997.
[51] Int. Cl.$^6$ .................................................. D06M 10/06
[52] U.S. Cl. ..................................................... 8/137; 134/6
[58] Field of Search ................................ 134/6; 510/278; 424/76.2, 76.8, 76.4, 682, 697; 8/137

[56] References Cited

U.S. PATENT DOCUMENTS

| | | |
|---|---|---|
| 1,615,146 | 1/1927 | Spindler ........................................ 8/137 |
| 1,633,213 | 6/1927 | Knig ............................................. 8/137 |
| 1,986,286 | 1/1935 | Ratzkoff ........................................ 8/137 |
| 2,379,458 | 7/1945 | Robinson ...................................... 8/137 |
| 3,436,772 | 4/1969 | Stebbins . | |
| 3,600,325 | 8/1971 | Kaufman et al. . | |
| 4,082,223 | 4/1978 | Nozawa . | |
| 4,161,288 | 7/1979 | McKinney . | |
| 4,274,560 | 6/1981 | Cater . | |
| 4,434,917 | 3/1984 | Saito et al. . | |
| 4,735,347 | 4/1988 | Schultz et al. . | |
| 4,819,835 | 4/1989 | Tasaki . | |
| 4,895,279 | 1/1990 | Schultz . | |
| 5,111,971 | 5/1992 | Winer . | |
| 5,232,126 | 8/1993 | Winer . | |
| 5,303,867 | 4/1994 | Peterson . | |

*Primary Examiner*—Jill Warden
*Assistant Examiner*—Yolanda E. Wilkins
*Attorney, Agent, or Firm*—Conley, Rose & Tayon, PC; Eric B. Meyertons

[57] ABSTRACT

An odor-removal composition and a method and system for applying the odor-removal composition to a material for removing odors or reducing the emanation of odors from the material are provided. The odor-removal composition includes a magnesium salt mixed in water at a concentration less than the solubility limit of magnesium salt. The odor-removal composition is preferably sprayed on a material that exhibits unwanted odors and in particular on fabric or hair that exhibits tobacco-smoke odors. The odor-removal composition may interact with substances that cause such odors to form molecules that have less foul odors or no odors.

64 Claims, 1 Drawing Sheet

METHOD COMPOSITION AND SYSTEM FOR REMOVING

PRIORITY CLAIM

This application claims the benefit of U.S. Provisional Application No. 60/044,200 entitled "Odor Removal Mixture," filed Apr. 8, 1997.

BACKGROUND OF THE INVENTION

1. Field of the Invention

The present invention generally relates to odor removal. More particularly, the invention relates to an odor-removal composition, a system for odor removal, and a method that may be used to remove odors from materials.

2. Description of the Related Art

Unappealing odors are present in all places of society. For example, materials that are exposed to tobacco smoke often naturally absorb and outgas smoke. Because such odors are objectionable and may make the environment seem unpleasant, various compositions have been developed for reducing odors. Many of these compositions, however, only substitute other odors for foul odors. Aromas or perfumes may be used to mask foul odors. While an aroma added to a foul odor may be inviting to some people, it may be disliked by other people. Further, the addition of such an aroma to undesirable odors may create another smell that is more disliked than the original odor.

The control of malodor has also involved chemical modification methods. Conventional chemical modification methods utilize oxidative agents such as oxygen bleaches, chlorine, sodium hypochlorite, chlorine dioxide, and potassium permanganate to reduce foul odors via oxidative degradation. Reductive degradation which uses reducing agents such as sodium bisulfite has also been employed to reduce malodor. Unfortunately, these types of oxidative agents and reducing agents may damage colored fabrics by bleaching and/or discoloring the colored fabrics. Odor absorption has also become a popular form of reducing odors. Commonly known odor absorbers include activated charcoal and zeolites. Unfortunately, these solids are harmful to fabrics. Activated charcoal may stain light colored fabrics, and zeolites may roughen the texture of the fabric if too much is applied to the fabric.

SUMMARY OF THE INVENTION

A method, composition, and/or system may be used to remove odors such as smoke odors. The odor-removing composition may include a magnesium-containing salt mixed in water. In one embodiment, the odor-removing composition contains magnesium sulfate mixed in purified water. The concentration of the magnesium salt in the water is preferably selected to be less than the magnesium salt's solubility limit. For purposes of this application, "solubility limit" refers to the maximum amount of a material that may be mixed in the water under the conditions at which the odor-removal composition is prepared. The solubility limit may vary as a function of, e.g., temperature and pressure. In addition, the concentration of other components present in a solution (e.g., added fragrance) may affect the solubility limit of the magnesium salt. Magnesium sulfate has a solubility limit in water of about 25 weight % at room temperature. Preferably, the concentration of magnesium sulfate in purified water is about 3% by weight, which appears to be the approximate concentration for optimum reduction of smoke odor emanation. The odor-removal composition may be applied to an odorous material that is a source of unwanted odors by, e.g., spraying the odor-removal composition on the odorous material. The odor-removal composition preferably interacts with substances in the odorous material, and thereby removes sources of odors, or reduces emanation of odors associated with these substances, from the material.

DETAILED DESCRIPTION OF THE PREFERRED EMBODIMENTS

Figure 1:
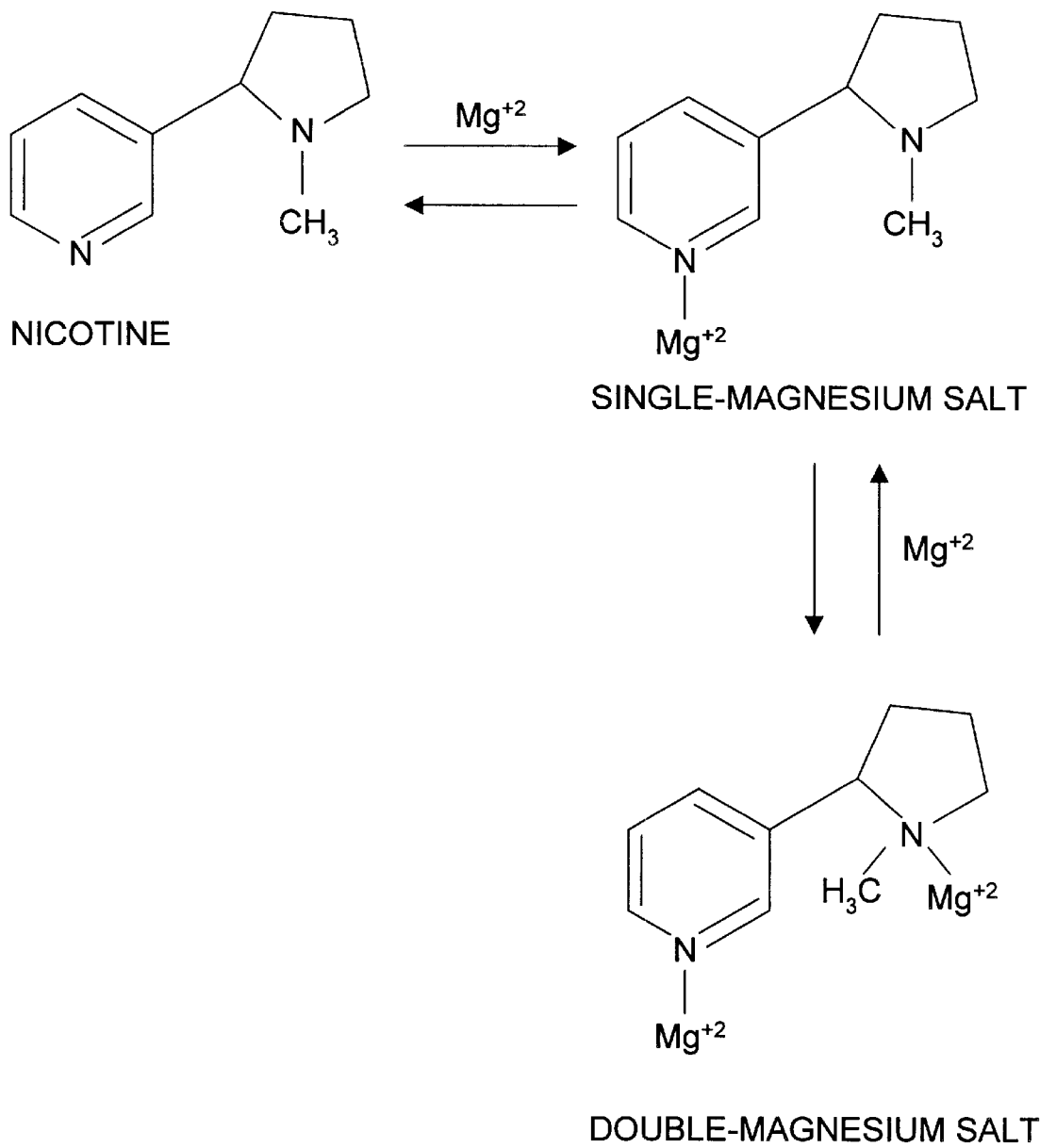
FIG. 1 depicts a proposed mechanism by which magnesium cations react with nicotine to form a substantially non-volatile salt.

In an embodiment, a composition for removing odors or reducing sources of odors from a material comprises a magnesium salt (e.g., magnesium sulfate, magnesium sulfite, magnesium chloride, magnesium nitrate) mixed in water. In a presently preferred embodiment, the magnesium salt is magnesium sulfate. Purified water (prepared by, e.g., distillation, reverse osmosis, or filtration) is preferably used because it contains fewer impurities that might reduce the effectiveness of the odor-removal composition. For example, certain impurities may cause algae to grow in the odor-removal composition. Thus, the use of purified water may extend the life of the odor-removal composition. It is believed that as long as the odor-removal composition remains sealed within a container away from ambient impurities, the shelf life of the odor-removal composition is quite long, and, in some circumstances, the shelf life may be virtually unlimited.

The amount of magnesium sulfate mixed in the water is preferably less than the solubility of magnesium sulfate in water (about 25 weight % at room temperature). As such, a solid residue is less likely to form upon the odorous material to which the odor removal composition is applied. Preferably, the concentration of magnesium sulfate in water is less than about 12 weight %, and more preferably less than about 5 weight % (e.g., about 1–5 weight %). Compositions containing higher concentrations of magnesium sulfate in water do not seem to be any more effective at reducing foul odors than the odor-removal composition containing about 3 weight % magnesium sulfate in water, which is a concentration at which the odor-removal composition is most effective at removing or reducing odors. Less-concentrated solutions may not remove or reduce odors as well as the 3weight % solution. An odor removal solution containing a magnesium sulfate concentration as low as about 1weight % may, however, be used to effectively alleviate odors, especially if applied repeatedly to an odorous material.

EXAMPLE

Concentrations of 3%, 4%, 5%, 7.5%, 10%, 15%, and 20% by weight of magnesium sulfate in water were prepared to determine at what point residues would be perceived by either touch or sight. The solutions were placed in 3-oz. pump spray bottles. Each spray from the bottles yielded about 180 microliters of fluid. To subjectively verify the concentrations, samples from each bottle were sprayed onto a clear glass window surface to observe for opacity.

The test solutions were applied to fabric samples including both natural and synthetic fibers in a variety of colors and textures, as shown in the table below. The spray bottles were primed by spraying two to three times before applying the solutions to the fabric samples. The spray bottles were then held vertically at a distance of about 15 cm from the fabric samples and either 2, 4, or 8 sprays applied to the samples. One spray created a fairly evenly dispersed circular pattern about 12 cm in diameter. Each application consisted of 2 sprays to a given area followed by 2 more sprays in an area adjacent to and below the initial area. A fan was used to facilitate drying of the samples following application of the test solutions.

Each sample was visually inspected using a scale of 0 to 10 to determine the amount of residue perceptible on the samples, with 0 representing "nothing seen" and 10 representing "caked material easily seen." Tactile inspection was also performed using a scale of 0 to 10 to determine the effect of the sample application of fabric texture, with 0 denoting "nothing perceived" and 10 denoting "starched/ stiff or palpable residue." Results of the tests are depicted in the table below.

As can be seen from the table, residue formed by evaporation of the solutions was found to be most prominent on dark fabrics and on those of solid coloring. There was no appreciable difference between natural and synthetic fabrics having similar coloration. Shiny fabrics such as nylon appeared highly susceptible to stiffness, while solid-colored wools showed the most visible residue. A 4 weight % solution was found to be the highest concentration which left no perceptible visual or tactile residue on any of the fabric samples tested following application of 2 sprays (about 360 microliters) of solution.

composition. In yet another embodiment, the odor removal composition may include aloe vera.

In still another embodiment, the odor-removal composition may include a perfume or fragrance. Suitable fragrances include essential oils of animal (e.g., natural musk) or plant (e.g., eugenol, geraniol) origin as well as components of essential oils, and analogs and derivatives of the components, which are synthetic. Because the odor-removal composition acts to remove or reduce the emanation of odors from an odiferous material, the added fragrance does not serve primarily as an odor-masking agent. As such, the addition of the fragrance to the odor-removal composition is less likely to result in the creation of unpleasant odors caused by mixing the fragrance with the odor-causing substance in the material.

The odor-removal composition may contain an anti-static agent. Preferred antistatic agents are water-soluble and include monoalkyl cationic quaternary ammonium compounds such as hydroxycetyl hydroxyethyl dimethyl ammonium chloride (DEHYQUART E, available from Henkel); polyethylene glycols; and polymeric quaternary ammonium salts such as MIRAPOL A-15 and MIRAPOL AD-1 (available rom Rhône-Poulenc). The odor-removal composition may also contain a solubilizing gent to solubilize any hydrophobic material, such as a perfume or fragrance, present in the odor-removal composition. The solubilizing agent may be a low-foaming or non-foaming surfactant such as the PLURONIC surfactants available from BASF; the Results reported as (visual; tactile)
0 = nothing detected, 10 = significant amounts detected

| Concentration (wt %) | Sprays per Area | 100% Cotton (Orange) | 50/50 Cotton/ Polyester (Flowered) | 100% Wool (Red) | 100% Rayon (Yellow) | 100% Cotton (Black) | 100% Wool (Black) | 100% Nylon (Dark Blue) |
|---|---|---|---|---|---|---|---|---|
| 3 | 2 | (0;0) | (0;0) | (0;0) | (0;0) | (0;0) | (0;0) | (0;0) |
|   | 4 | (0;0) | (0;0) | (0;0) | (0;0) | (0;0) | (0;0)* | (1;5) |
|   | 8 | (0;0) | (0;0) | (0;0) | ND | ND | ND | ND |
| 4 | 2 | (0;0) | (0;0) | (0;0) | (0;0) | (0;0) | (0;0) | (0;0) |
|   | 4 | (0;0) | (0;0) | (1;0) | (0;0) | (0;0) | (1;0) | (1;5) |
|   | 8 | (0;0) | (0;0) | (0;0) | ND | ND | ND | ND |
| 5 | 2 | (0;0) | (0;0) | (0;0) | (0;0) | (0;0) | (0;0)* | (0;0)* |
|   | 4 | (0;0) | (0;0) | (1;0) | (0;0) | (0;0) | (1;0) | (1;5) |
|   | 8 | (0;0) | (0;0) | (3;0) | ND | ND | ND | ND |
| 7.5 | 2 | (0;0) | (0;0) | (0;0) | (0;0) | (0;0)* | (0;0)* | (1;1) |
|   | 4 | (0;0) | (0;0) | (2;0) | (0;0) | (0;1)* | (2;0) | (2;6) |
|   | 8 | (0;0) | (0;0) | (4;0) | ND | ND | ND | ND |
| 10 | 2 | (0;0) | (0;0) | (1;0) | (0;0) | (0;0)* | (1;0) | (1;2) |
|   | 4 | (0;0) | (0;0) | (3;0) | (0;0) | (1;2) | (3;0) | (3;6) |
|   | 8 | (0;0) | (0;0) | (5;0) | ND | ND | ND | ND |
| 15 | 2 | (0;0) | (0;0) | (3;0) | (0;0) | (1;0) | (1;1) | (1;2) |
|   | 4 | (0;0) | (0;1) | (5;1) | (0;0) | (3;5) | (5;1) | (4;7) |
|   | 8 | (0;0) | (0;5) | (8;5) | ND | ND | ND | ND |
| 20 | 2 | (0;0) | (0;0) | (5;1) | (0;0) | (1;0) | (3;1) | (2;3) |
|   | 4 | (0;0) | (0;2) | (6;1) | (0;0) | (4;5) | (5;1) | (4;8) |
|   | 8 | (0;5) | (0;5) | (8;5) | ND | ND | ND | ND |

ND = Not Done
*= visible when touched

In another embodiment, the odor removal composition may contain preservatives in addition to magnesium sulfate and water. For example, the odor removal composition may comprise 0.05 weight % KATHON CG, a preservative commercially available from Rohm and Haas Company. The odor removal composition may also comprise 0.3% DMDM HYDANTOIN, commercially available from McIntyre Group Ltd. The preservatives may function as anti-microbial (e.g., anti-fungal and/or anti-bacterial) agents. The preservatives may help extend the shelf life of the odor-removal SURFYNOL surfactants available from Air Products; and the IGEPAL surfactants available from Rhône-Poulenc.

In an embodiment, the above described composition may be applied to a material to remove odors or reduce emanation of odors (e.g., tobacco smoke or gasoline odors) from the odorous material. Examples of materials to which the odor-removal composition may be applied to achieve such effects include, but are not limited to, fabrics (e.g., clothing, furniture upholstery, carpets, rugs, automobile upholstery, automobile carpet, draperies, curtains); hair; leather, and sheet rock and building materials (e.g., concrete, plaster, wood, and other porous materials). Preferably, the odor-removal composition causes no substantial discoloration of the material to which the composition is applied. The odor-removal composition should cause no substantial discoloration of the material both during use (i.e., when the composition is applied to the material and allowed to dry) and after use (e.g., when the material is washed or dry-cleaned).

The odor-removal composition may be stored in various sized containers until it is used. Preferably, the odor removal composition is applied to odorous materials within a few hours after exposure to the source of the odor. Different methods may be employed to apply the odor removal composition to the surface of an odorous material. In one embodiment, a brush may be dipped into the odor-removal composition while it is in its storage container. The brush may then be used to apply the odor-removal composition to the targeted material. A cloth may be used to apply the odor-removal composition to targeted materials in a similar manner.

In an embodiment, the odor-removal composition may be contained within a spray dispenser. The spray dispenser may be an aerosol dispenser such as those described in U.S. Pat. No. 3,436,772 issued to Stebbins and U.S. Pat. No. 3,600,325 issued to Kaufman et al., both of which are incorporated herein by reference as if fully set forth. Preferably, the aerosol dispenser includes a container for holding the odor-removal composition and a valve member which will permit the odor-removal composition to be applied to the material containing the odorous material as a spray of fine, or finely divided, particles or droplets. The container is preferably sealed and pressurized by incorporating a gaseous propellant therein. Depression of an actuator coupled to the valve member causes the odor-removal composition within the container to be dispensed. Commonly used propellants include gaseous hydrocarbons, such as isobutane, and mixed halogenated hydrocarbons. Because the use of hydrocarbon propellants is believed to be environmentally deleterious, alternative propellants such as compressed air, nitrogen, carbon dioxide, and inert gases are generally preferred.

In an alternative embodiment, the odor-removal composition may be contained within a self-pressurized, non-aerosol container that includes a convoluted liner and an elastomeric sleeve. The container may include a liner/sleeve assembly containing a thin flexible radially expandable convoluted plastic liner inside an essentially cylindrical sleeve. Examples of such a container may be found in U.S. Pat. No. 5,111,971 issued to Winer and in U.S. Pat. No. 5,232,126 issued to Winer, both of which are incorporated by reference as if fully set forth herein.

In an alternative embodiment, the odor-removal composition may be placed within a manually activated spray dispenser. The spray dispenser may be any of the known manually activated dispensers which are used to produce a spray of liquid droplets. The spray dispenser is preferably a non-aerosol, manually activated, pump-spray dispenser. The pump-spray dispenser may include a pump chamber having an opening at one end. A pump stem and piston assembly may be disposed within the pump chamber for reciprocal motion within the chamber. A passageway through which liquid may pass preferably extends through the pump stem, terminating in a dispensing outlet of a spray nozzle. The odor removal composition may be pumped from the pump chamber and out through the spray nozzle. The spray nozzle is preferably positioned about 8–12 inches away from the targeted material prior to spraying a mist of the odor removal composition from the dispenser. The following patents, which are incorporated by reference as if fully set forth herein, describe in detail different types of pump-spray dispensers: U.S. Pat. No. 4,895,279 to Schultz; U.S. Pat. No. 4,735,347 to Schultz et al.; and U.S. Pat. No. 4,274,560 to Carter.

Alternately, the spray dispenser may be a manually activated trigger-spray dispenser. The trigger-spray dispenser preferably does not incorporate a propellant gas into the odor removal composition. The dispenser includes a trigger mechanism, e.g., a piston or collapsing bellows, for displacing the odor-removal composition through a nozzle to create a spray of liquid. The trigger-spray dispenser may include a pump chamber having a piston or bellows disposed therein. In response to the piston or bellows being compressed the pressure on the odor-removal composition within the pump chamber is increased, causing an outlet check valve to open. The odor-removal composition is then allowed to flow through the check valve and out a nozzle. For detailed descriptions of various types of trigger-spray dispensers, see U.S. Pat. No. 4,082,223 to Nozawa, U.S. Pat. No. 4,161,288 to McKinney, U.S. Pat. No. 4,434,917 to Saito et al., U.S. Pat. No. 4,819,835 to Tasaki, and U.S. Pat. No. 5,303,867 to Peterson, all of which are incorporated by reference as if fully set forth herein.

The odor-removal compound may reduce emanation of odors from a material to which it is applied by interacting with at least one odor-causing compound present in the material. A major odor component of tobacco smoke is nicotine. Other types of odor-causing molecules in tobacco smoke include pyrazines, phenols, cresols, and pyridine derivatives other than nicotine. The nicotine molecules contains a pyridine nitrogen atom and a tertiary amine atom. Both of these nitrogen atoms are Lewis Bases and are expected to coordinate with Lewis Acids. The divalent magnesium cation is a Lewis Acid and is expected to coordinate with both of the nitrogen atoms in the nicotine molecule. Magnesium ions are thought to form a salt with odor-causing Lewis Base components of tobacco smoke. Since these salts are non-volatile, they should not contribute to the production of odors.

When coordination between the magnesium cation and one or more of the nitrogen atoms in the nicotine molecule occurs, the resulting complex formed will have a formal positive charge of +1 on the coordinated nitrogen atom(s). This coordination will increase the effective electronegativity of the coordinated nitrogen atoms(s), which will in turn withdraw electron density from other atoms in the molecule by resonance and/or inductive effects. This change in electron density that results from Lewis Acid/Base complex formation may, in principle, be monitored by Proton Nuclear Magnetic Resonance ($H^1NMR$) spectroscopy because the resonance absorbance frequency of NMR active atomic nuclei is dependent upon the electron density around the nucleus. As the electron density around an atomic nucleus decreases, the shielding of the nucleus from the applied external magnetic field decreases and the absorption position of that nucleus will shift down-field.

Because of the potential observable causal relationship between, on the one hand, the formation of a Lewis Acid/Base salt between nicotine and $Mg^{+2}$, and, on the other hand, the position of the NMR resonance frequencies of the protons in the nicotine molecule, it may be possible to use H¹NMR to test for adduct formation between nicotine and Mg$^{+2}$. Proof of such adduct formation should lend support for the above proposed deodorizing mechanism of magnesium sulfate.

To test this belief, a 0.23 millimolar solution of nicotine was prepared in deuterated water (D$_2$O) with 0.05 weight % 3-(trimethylsilyl)-propionic-2,2,3,3,-d$_4$ acid, sodium salt as the internal reference standard. To the nicotine solution was added MgSO$_4$ at a 0, 0.115, 0.23, 0.46, or 0.92 millimolar (mM) concentration. Because sodium cations, unlike magnesium cations, are non-complexing ions, a nicotine sample to which NaCl was added at a 0.46 millimolar (mM) concentration was used as a control sample. The NaCl was used as a control to show that a down-field shift is not caused by the addition of the non-complexing ion but requires the formation of the magnesium-nicotine salt. If Lewis Acid/Base adducts are being formed between nicotine and Mg$^{+2}$ cations, then, as the molar ration of nicotine to the magnesium cation is changed from 1:0 to 1:0.5 to 1:1 to 1:2 to 1:5, the solution upon which the H¹NMR is being run should change from being a pure solution of just one component (nicotine) to a mixture of nicotine and both its single- and double-magnesium salts, depicted in FIG. 1. As the concentration of added magnesium is increased, the amount of the double-magnesium nicotine salt may increase until it is the only nicotine-containing species present. This increase in the amount of the double-magnesium salt present will tend to be manifested in an increased down-field shift in the nicotine H¹NMR spectrum in one of two ways.

If the equilibrium between nicotine and its two magnesium salts is slow on the NMR time scale, the series of NMR spectra should begin with the spectrum of pure nicotine and then proceed through a sequence of complex spectra consisting of the H¹NMR spectra of each separate component (i.e., nicotine, single-magnesium salt, and double-magnesium salt) superimposed on the same spectrum printout. Each of the components should have a peak intensity in the superimposed spectra proportional to the concentration of the component in the solution. Eventually, when the Mg$^{-2}$ concentration is great enough so that the double-magnesium salt is essentially the only chemical species present, the H¹NMR spectrum should simplify to resemble the original H¹NMR spectrum of pure nicotine, except shifted downfield from the H¹NMR of pure nicotine.

If the equilibrium between nicotine and its two magnesium salts is fast on the NMR time scale, the series of NMR spectra should begin with the spectrum of pure nicotine and then proceed through a sequence of spectra consisting of the average H¹NMR spectra of each separate component (i.e., nicotine, single-magnesium salt, and double-magnesium salt) proportional to its concentration in solution. Eventually, when the Mg$^{+2}$ concentration is great enough so that the double-magnesium salt is essentially the only chemical species present, the H¹NMR spectrum should simplify to resemble the original H¹NMR spectrum of pure nicotine, except shifted downfield from the H¹NMR of pure nicotine. In this case, all of the H¹NMR spectra should look alike, but they will appear to slowly move downfield as the ratio of magnesium cation to nicotine is increased.

Sample analysis was performed and 300 MHz Fourier Transform H¹NMR spectra obtained by the NMR Laboratory at the University of Minnesota. Results of the experiments are shown in the following table:

| Nicotine Concentration | Added Salt | Amine Proton Absorbance | Meta Pyridine Proton Absorbance |
|---|---|---|---|
| 0.23 mM | NONE | 2.103 | 7.476 |
| 0.23 mM | 0.115 mM MgSO$_4$ | 2.114 | 7.481 |
| 0.23 mM | 0.23 mM MgSO$_4$ | 2.115 | 7.483 |
| 0.23 mM | 0.46 mM MgSO$_4$ | 2.120 | 7.487 |
| 0.23 mM | 0.92 mM MgSO$_4$ | 2.170 | 7.519 |
| 0.23 mM | 0.46 mM NaCl | 2.102 | 7.480 |

The experimental results show a gradual down-field shift with increasing Mg$^{+2}$ ion concentration for both the tertiary amine proton absorbance position and for the absorbance position for the aromatic ring proton meta to the pyridine nitrogen. In contrast, the absorbance spectra for the samples to which NaCl was added are essentially identical to the samples containing pure nicotine and no added salts. The down-field shift in the H¹NMR spectra of the nicotine protons in samples containing added Mg$^{+2}$ suggests that adduct formation is occurring between the magnesium and the nicotine in a concentration-dependent manner. To the extent that nicotine exists as a salt, it is non-volatile and does not contribute to smoke odor. The degree of odor attenuation should be dependent upon the concentration of magnesium applied.

Further modifications and alternative embodiments of various aspects of the invention will be apparent to those skilled in the art in view of this description. For example, additional components may be added to the odor removal composition to improve the quality of the odor-removal composition. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for removing tobacco smoke odors from fabric, comprising:

applying an odor-removal composition to the fabric, wherein the odor-removal composition comprises a magnesium salt mixed in water at a concentration less than a solubility limit of the magnesium salt in the water;

allowing the odor-removal composition to dry such that substantially no residue is visible upon the fabric; and allowing the odor-removal composition to interact with at least one odor-causing compound that causes tobacco smoke odors in the fabric, thereby reducing the emanation of odors from the fabric.

2. A method for removing tobacco smoke odors from fabric, comprising:

applying an odor-removal composition to the fabric, wherein the odor-removal composition comprises magnesium sulfate mixed in purified water, wherein the magnesium sulfate is mixed at a concentration of less than approximately 12 weight % in the purified water;

allowing the odor-removal composition to dry such that substantially no residue is visible upon the fabric; and allowing the odor-removal composition to interact with at least one odor-causing compound that causes tobacco smoke odors in the fabric, thereby reducing the emanation of odors from the fabric.

3. The method of claim 2 wherein the concentration of the magnesium sulfate is less than approximately 5 weight % in the purified water.

4. The method of claim 2 wherein the concentration of the magnesium sulfate is approximately 3 weight % in the purified water.

5. The method of claim 2 wherein the concentration of the magnesium sulfate in the purified water is sufficient to facilitate formation of a non-volatile salt of magnesium with odor-causing molecules.

6. The method of claim 2, further comprising allowing the odor-removal composition to dry such that substantially no tactilely detectable residue is formed on the fabric.

7. The method of claim 2 wherein the odor-removal composition further comprises a preservative compound for extending the life of the odor-removal composition.

8. The method of claim 2 wherein the odor-removal composition further comprises a preservative compound, and wherein the preservative compound comprises an antimicrobial agent.

9. The method of claim 2 wherein the odor-removal composition further comprises a fragrance.

10. The method of claim 2 wherein the odor-removal composition further comprises an anti-static agent.

11. The method of claim 2 wherein the odor-removal composition further comprises aloe vera.

12. The method of claim 2 wherein the odor-removal composition further comprises a solubilizing agent.

13. The method of claim 2 wherein applying the odor-removal composition comprises pumping the odor-removal composition from a container toward the fabric.

14. The method of claim 13 wherein the container is a pump-spray dispenser.

15. The method of claim 13 wherein the container is a trigger-spray dispenser.

16. The method of claim 2 wherein applying the odor-removal composition comprises spraying the odor-removal composition from a container toward the fabric.

17. The method of claim 16 wherein the container is an aerosol spray dispenser.

18. The method of claim 16 wherein the container is a self-pressurized, non-aerosol spray dispenser.

19. The method of claim 2 wherein applying the odor-removal composition comprises placing the odor-removal composition on a brush and transferring the odor-removal composition from the brush to the fabric.

20. The method of claim 2 wherein applying the odor-removal composition comprises placing the odor-removal composition on a cloth and transferring the odor-removal composition from the cloth to the fabric.

21. The method of claim 2 wherein the fabric is selected from the group consisting of clothing, furniture upholstery, curtains, and drapery.

22. The method of claim 2 wherein the fabric is selected from the group consisting of automobile upholstery and automobile carpet.

23. The method of claim 2 wherein the fabric is selected from the group consisting of carpeting and rugs.

24. The method of claim 2 wherein reducing the emanation of odors comprises forming a non-volatile salt between magnesium cations and odor-causing molecules.

25. The method of claim 24 wherein the odor-causing molecules comprise nicotine.

26. The method of claim 2 wherein the odor-removal composition further comprises a preservative compound for extending the life of the odor-removal composition and wherein the concentration of the magnesium sulfate mixed in the purified water is sufficient to facilitate formation of a non-volatile salt of magnesium with odor-causing molecules.

27. The method of claim 2 wherein the odor-removal composition causes no substantial discoloration of the fabric.

28. A method for removing tobacco smoke odors from hair, comprising:

applying an odor-removal composition to the hair, wherein the odor-removal composition comprises a magnesium salt mixed in water at a concentration less than a solubility limit of the magnesium salt in the water;

allowing the odor-removal composition to dry such that substantially no residue is visible upon the hair; and allowing the odor-removal composition to interact with at least one odor-causing compound that causes tobacco smoke odors in the hair, thereby reducing the emanation of odors from the hair.

29. A method for removing tobacco smoke odors from hair, comprising:

applying an odor-removal composition to the hair, wherein the odor-removal composition comprises magnesium sulfate mixed in purified water, wherein the magnesium sulfate is mixed at a concentration of less than approximately 12 weight % in the purified water;

allowing the odor-removal composition to dry such that substantially no residue is visible upon the hair; and allowing the odor-removal composition to interact with at least one odor-causing compound that causes tobacco smoke odors in the hair, thereby reducing the emanation of odors from the hair.

30. A method for removing odors from material, comprising:

applying an odor-removal composition to the material, wherein the odor-removal composition comprises a magnesium salt mixed in water at a concentration less than a solubility limit of the magnesium salt in the water; and allowing the odor-removal composition to interact with at least one odor-causing compound that causes in the material, thereby reducing the emanation of odors from the material.

31. The method of claim 30, further comprising allowing the odor-removal composition to dry such that substantially no residue is visible upon the material.

32. The method of claim 30 wherein the odor-removal composition causes no substantial discoloration of the material.

33. A method for removing odors from material, comprising:

applying an odor-removal composition to the material, wherein the odor-removal composition comprises magnesium sulfate mixed in water at a concentration less than a solubility limit of the magnesium sulfate in the water;

allowing the odor-removal composition to interact with at least one odor-causing compound that causes in the material, thereby reducing the emanation of odors from the material.

34. The method of claim 33, further comprising allowing the odor-removal composition to dry such that no residue is visible upon the material.

35. The method of claim 33 wherein the concentration of the magnesium sulfate is less than approximately 12 weight % in the water.

36. The method of claim 33 wherein the concentration of the magnesium sulfate is less than approximately 5 weight % in the water.

37. The method of claim 33 wherein the concentration of the magnesium sulfate is approximately 3 weight % in the water.

38. The method of claim 33 wherein the water is purified water.

39. The method of claim 33 wherein the concentration of magnesium sulfate in the water is sufficient to facilitate formation of a non-volatile salt of magnesium with odor-causing molecules.

40. The method of claim 33, further comprising allow the odor-removal composition to dry such that substantially no tactilely detectable residue is formed on the material.

41. The method of claim 33 wherein the odor-removal composition further comprises a preservative compound for extending the life of the odor-removal composition.

42. The method of claim 33 wherein the odor-removal composition further comprises a preservative compound, and wherein the preservative compound comprises an anti-microbial agent.

43. The method of claim 33 wherein the odor-removal composition further comprises a fragrance.

44. The method of claim 33 wherein the odor-removal composition further comprises an anti-static agent.

45. The method of claim 33 wherein the odor-removal composition further comprises aloe vera.

46. The method of claim 33 wherein the odor-removal composition further comprises a solubilizing agent.

47. The method of claim 33 wherein applying the odor-removal composition comprises pumping the odor-removal composition from a container toward the material.

48. The method of claim 47 wherein the container is a pump-spray dispenser.

49. The method of claim 47 wherein the container is a trigger-spray dispenser.

50. The method of claim 33 wherein applying the odor-removal composition comprises spraying the odor-removal composition from a container toward the material.

51. The method of claim 50 wherein the container is an aerosol spray dispenser.

52. The method of claim 50 wherein the container is a self-pressurized, non-aerosol spray dispenser.

53. The method of claim 33 wherein applying the odor-removal composition comprises placing the odor-removal composition on a brush and transferring the odorremoval composition from the brush to the material.

54. The method of claim 33 wherein applying the odor-removal composition comprises placing the odor-removal composition on a cloth and transferring the odor-removal composition from the cloth to the material.

55. The method of claim 33 wherein the material is selected from the group consisting of clothing, furniture upholstery, curtains, and drapery.

56. The method of claim 33 wherein the material is selected from the group consisting of automobile upholstery and automobile carpet.

57. The method of claim 33 wherein the material is selected from the group consisting of carpeting and rugs.

58. The method of claim 33 wherein the material is selected from the group consisting of building materials and sheetrock.

59. The method of claim 33 wherein the material is hair.

60. The method of claim 33 wherein the material is leather.

61. The method of claim 33 wherein reducing the emanation of odors comprises forming a non-volatile salt between magnesium cations and odor-causing molecules.

62. The method of claim 61 wherein the odor-causing molecules comprise nicotine.

63. The method of claim 33 wherein the odor-removal composition further comprises a preservative compound for extending the life of the odor-removal composition and wherein the concentration of the magnesium sulfate in the water is sufficient to facilitate formation of a non-volatile salt of magnesium with odor-causing molecules.

64. The method of claim 33 wherein the odor-removal composition causes no substantial discoloration of the material.

\* \* \* \* \*

UNITED STATES PATENT AND TRADEMARK OFFICE
CERTIFICATE OF CORRECTION

PATENT NO. : 5,976,193

DATED : November 2, 1999

INVENTOR(S) : Sherrie L. Thomas, Paul F. Lane

It is certified that error appears in the above-identified patent and that said Letters Patent is hereby corrected as shown below:

On the title page item [54], should read

--METHOD, COMPOSITION, AND SYSTEM FOR REMOVING ODORS--

Signed and Sealed this

Fifth Day of September, 2000

Attest:

Q. TODD DICKINSON

*Attesting Officer*  *Director of Patents and Trademarks*